(12) United States Patent
Nayeri et al.

(10) Patent No.: US 10,551,327 B2
(45) Date of Patent: Feb. 4, 2020

(54) COOLING HOLE INSPECTION SYSTEM

(71) Applicant: General Electric Company, Schenectady, NY (US)

(72) Inventors: Majid Nayeri, Niskayuna, NY (US); Michael Lexa, Niskayuna, NY (US); Byron Knight, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 73 days.

(21) Appl. No.: 15/950,894

(22) Filed: Apr. 11, 2018

(65) Prior Publication Data
US 2019/0317025 A1 Oct. 17, 2019

(51) Int. Cl.
| | |
|---|---|
| G01M 15/14 | (2006.01) |
| G01N 21/956 | (2006.01) |
| G01N 25/72 | (2006.01) |
| F01D 21/00 | (2006.01) |
| F01D 5/14 | (2006.01) |
| F01D 5/18 | (2006.01) |
| G01N 21/88 | (2006.01) |

(52) U.S. Cl.
CPC ....... *G01N 21/95692* (2013.01); *F01D 5/147* (2013.01); *F01D 5/189* (2013.01); *F01D 21/003* (2013.01); *G01M 15/14* (2013.01); *G01N 25/72* (2013.01); *F05D 2220/32* (2013.01); *F05D 2260/201* (2013.01); *F05D 2260/83* (2013.01); *G01N 2021/8887* (2013.01); *G01N 2201/102* (2013.01)

(58) Field of Classification Search
CPC .......... F01D 5/18; F01D 5/147; G01M 15/14; G01N 21/95692

USPC ....................................................... 73/112.01
See application file for complete search history.

(56) References Cited

U.S. PATENT DOCUMENTS

| | | |
|---|---|---|
| 4,644,162 A | 2/1987 | Bantel |
| 4,916,715 A | 4/1990 | Adiutori |

(Continued)

FOREIGN PATENT DOCUMENTS

| | | |
|---|---|---|
| DE | 10 2009 039 224 A1 | 3/2011 |
| DE | 10 2012 206 103 B3 | 7/2013 |

(Continued)

OTHER PUBLICATIONS

Bantel et al., "Automated Infrared Inspection of Jet Engine Turbine Blades", Thermosense VIII: Thermal Infrared Sensing for Diagnostics and Control, vol. 0581, Mar. 28, 1986.

(Continued)

*Primary Examiner* — Eric S. McCall
(74) *Attorney, Agent, or Firm* — Christopher R. Carroll; The Small Patent Law Group LLC

(57) ABSTRACT

An inspection system includes a thermographic sensor configured to capture thermographic data of a component having holes as a fluid is pulsed toward the holes, and one or more processors configured to temporally process the thermographic data to calculate temporal scores for the corresponding holes, spatially process the thermographic data to calculate spatial scores for the corresponding holes, and calculate composite scores associated with the holes based on the temporal scores and based on the spatial scores. The composite scores represent a likelihood that the corresponding holes are open, blocked or partially blocked.

21 Claims, 7 Drawing Sheets

(56) References Cited

U.S. PATENT DOCUMENTS

| | | | |
|---|---|---|---|
| 4,978,230 A | 12/1990 | Adiutori et al. | |
| 5,111,046 A | 5/1992 | Bantel | |
| 5,275,489 A | 1/1994 | Borneman et al. | |
| 5,562,345 A | 10/1996 | Heyman et al. | |
| 5,773,790 A | 6/1998 | Moore | |
| 6,422,743 B1 | 7/2002 | Nirmalan et al. | |
| 6,570,175 B2 | 5/2003 | Bales et al. | |
| 6,711,506 B2 | 3/2004 | Bales et al. | |
| 6,804,622 B2 | 10/2004 | Bunker et al. | |
| 7,651,261 B2 | 1/2010 | Bunker et al. | |
| 8,244,488 B2 | 8/2012 | Allen | |
| 8,287,183 B2 | 10/2012 | Shepard et al. | |
| 8,435,004 B1* | 5/2013 | Liang | F01D 5/187 416/92 |
| 8,449,176 B2 | 5/2013 | Shepard | |
| 8,498,836 B2 | 7/2013 | Carlson | |
| 8,810,644 B2 | 8/2014 | Bunker et al. | |
| 9,080,453 B2 | 7/2015 | Shepard et al. | |
| 9,310,312 B2 | 4/2016 | Jahnke et al. | |
| 9,470,605 B2 | 10/2016 | Koonankeil | |
| 2002/0187039 A1* | 12/2002 | Rinck | F01D 5/141 415/115 |
| 2002/0197159 A1* | 12/2002 | Roeloffs | F01D 5/186 416/92 |
| 2004/0037344 A1 | 5/2004 | Bunker et al. | |
| 2004/0262521 A1 | 12/2004 | Devitt et al. | |
| 2007/0209134 A1 | 9/2007 | Knopow et al. | |
| 2007/0237466 A1 | 10/2007 | Togami et al. | |
| 2009/0016402 A1 | 1/2009 | Bunker et al. | |
| 2009/0162209 A1* | 6/2009 | Wortman | F01D 5/187 416/241 R |
| 2009/0255332 A1 | 10/2009 | Bunker et al. | |
| 2009/0297336 A1 | 12/2009 | Allen et al. | |
| 2010/0235115 A1 | 9/2010 | Shepard | |
| 2010/0239412 A1* | 9/2010 | Draper | F01D 5/186 415/115 |
| 2010/0250155 A1 | 9/2010 | Bunker et al. | |
| 2011/0048117 A1 | 3/2011 | Kell et al. | |
| 2011/0125423 A1 | 5/2011 | Allen et al. | |
| 2011/0164653 A1 | 7/2011 | Allen et al. | |
| 2011/0235672 A1 | 9/2011 | Shepard et al. | |
| 2011/0251060 A1 | 10/2011 | Harrison et al. | |
| 2011/0267428 A1 | 11/2011 | George et al. | |
| 2012/0082567 A1* | 4/2012 | Tibbott | F01D 5/186 416/97 R |
| 2013/0041614 A1 | 2/2013 | Shepard et al. | |
| 2015/0000387 A1* | 1/2015 | Jiang | F01D 5/147 73/112.01 |
| 2015/0033836 A1 | 2/2015 | McCaldon | |
| 2016/0177772 A1 | 6/2016 | Smith et al. | |
| 2016/0252420 A1 | 9/2016 | Koonankeil | |
| 2019/0120066 A1* | 4/2019 | Buchal | F01D 5/186 |

FOREIGN PATENT DOCUMENTS

| | | |
|---|---|---|
| EP | 1227222 A2 | 7/2002 |
| EP | 1416266 A1 | 5/2004 |
| EP | 2518480 A1 | 10/2012 |
| EP | 2881731 A1 | 12/2014 |
| EP | 3273230 A1 | 7/2017 |
| FR | 2630209 A1 | 10/1989 |
| WO | 93/22663 A1 | 11/1993 |
| WO | 03/038238 A2 | 5/2003 |

OTHER PUBLICATIONS

Ding, "Test of Jet Engine Turbine Blades by Thermography", Optical Engineering, vol. 24, Issue: 06, Dec. 1, 1985.

Rosemau et al., "Aircraft Engine Blade Cooling Holes Detection and Classification from Infrared Images" Nondestructive Evaluation of Aging Aircraft, Airports, and Aerospace Hardware III, vol. 3586, Jan. 28, 1999.

Extended European Search Report dated Oct. 9, 2019 for corresponding EP Application No. 19167916.6.

* cited by examiner

COOLING HOLE INSPECTION SYSTEM

FIELD

The subject matter described herein relates to systems and methods that inspect holes or openings in objects for blockage, such as cooling holes in turbine blades.

BACKGROUND

Components of machines can experience extreme temperatures. For example, turbine blades in turbine engines can be exposed to extremely hot temperatures during operation of the engines. These blades can be provided with cooling holes that permit and direct the flow of a cooling fluid, such as cooler air, through and/or outside of the turbine blades. This cooling fluid can be directed outside of the blades by the cooling holes to provide a thermally protective barrier that prevents the blades from becoming too hot. Without the cooling holes, the turbine blades can prematurely fail.

Cooling holes may be completely or partially blocked. Completely blocked cooling holes do not allow for the cooling fluid to pass through the holes, while partially blocked cooling holes reduce the flow of the cooling fluid through the holes (relative to open holes that are not partially blocked). Partial or complete blockage of cooling holes can result in less cooling fluid being available to protect the components from thermal damage.

BRIEF DESCRIPTION

In one embodiment, a method for detecting blockage of holes in a component is provided. The method includes capturing thermographic data of the component and the holes as a fluid is pulsed toward the holes, temporally processing the thermographic data to calculate temporal scores for the corresponding holes, spatially processing the thermographic data to calculate spatial scores for the corresponding holes, and calculating composite scores associated with the holes based on the temporal scores and based on the spatial scores. The composite scores represent a likelihood that the corresponding holes are blocked.

In one embodiment, an inspection system includes a thermographic sensor configured to capture thermographic data of a component having holes as a fluid is pulsed toward the holes, and one or more processors configured to temporally process the thermographic data to calculate temporal scores for the corresponding holes, spatially process the thermographic data to calculate spatial scores for the corresponding holes, and calculate composite scores associated with the holes based on the temporal scores and based on the spatial scores. The composite scores represent a likelihood that the corresponding holes are blocked.

In one embodiment, a method for detecting blockage of cooling holes in a turbine blade is provided. The method includes capturing thermographic data of the turbine blade and the cooling holes as a fluid is pulsed toward the cooling holes, temporally processing the thermographic data to calculate temporal scores for the corresponding cooling holes, spatially processing the thermographic data to calculate spatial scores for the corresponding cooling holes, and calculating composite scores associated with the cooling holes based on the temporal scores and based on the spatial scores. The composite scores represent a likelihood that the corresponding cooling holes are blocked.

BRIEF DESCRIPTION OF THE DRAWINGS

The present inventive subject matter will be better understood from reading the following description of non-limiting embodiments, with reference to the attached drawings, wherein below.

DETAILED DESCRIPTION

One or more embodiments of the inventive subject matter described herein provide systems and methods that both spatially and temporally process thermographic image data to automatically detect blocked holes in components. In one embodiment, the holes that are examined are cooling holes in turbine blades, such as combustion state one blades. Alternatively, the holes that are examined may be other holes and/or holes in another component.

The systems and methods can examine statistical properties of infrared-based video signals of the components, use a customized image registration algorithm, and use a scoring fusion to automatically detect the blocked cooling holes in the turbine blade. The thermographic signals can be both temporally and spatially processed to identify which cooling holes are blocked. The temporal processing can include statistical signal processing for the thermographic signal history of pixels associated with the cooling holes. The spatial processing can include calculating aggregate likelihood scores for each cooling hole location based on the pixels that are occupied by the cooling hole in the thermographic signals. While the description herein focuses on the use of pixels in the processing of the thermographic data, optionally, another video or image data unit can be used, such as a voxel.

The systems and methods can capture thermographic (e.g., infrared) video sequences of turbine blades as a cooling fluid is repeatedly pulsed through cooling holes in the blades. The thermographic video sequences can be captured as video or image data, and the cooling fluid can be air that is periodically forced into the cooling holes. The systems and methods can use both spatial and temporal processing of the thermographic data to reduce the video data to a single normalized image. This single normalized image may be created for several cooling holes being examined, or may be created for a single cooling hole. The systems and methods can use the normalized image to calculate composite scores that are then used to determine whether a cooling hole is blocked.

Figure 1:
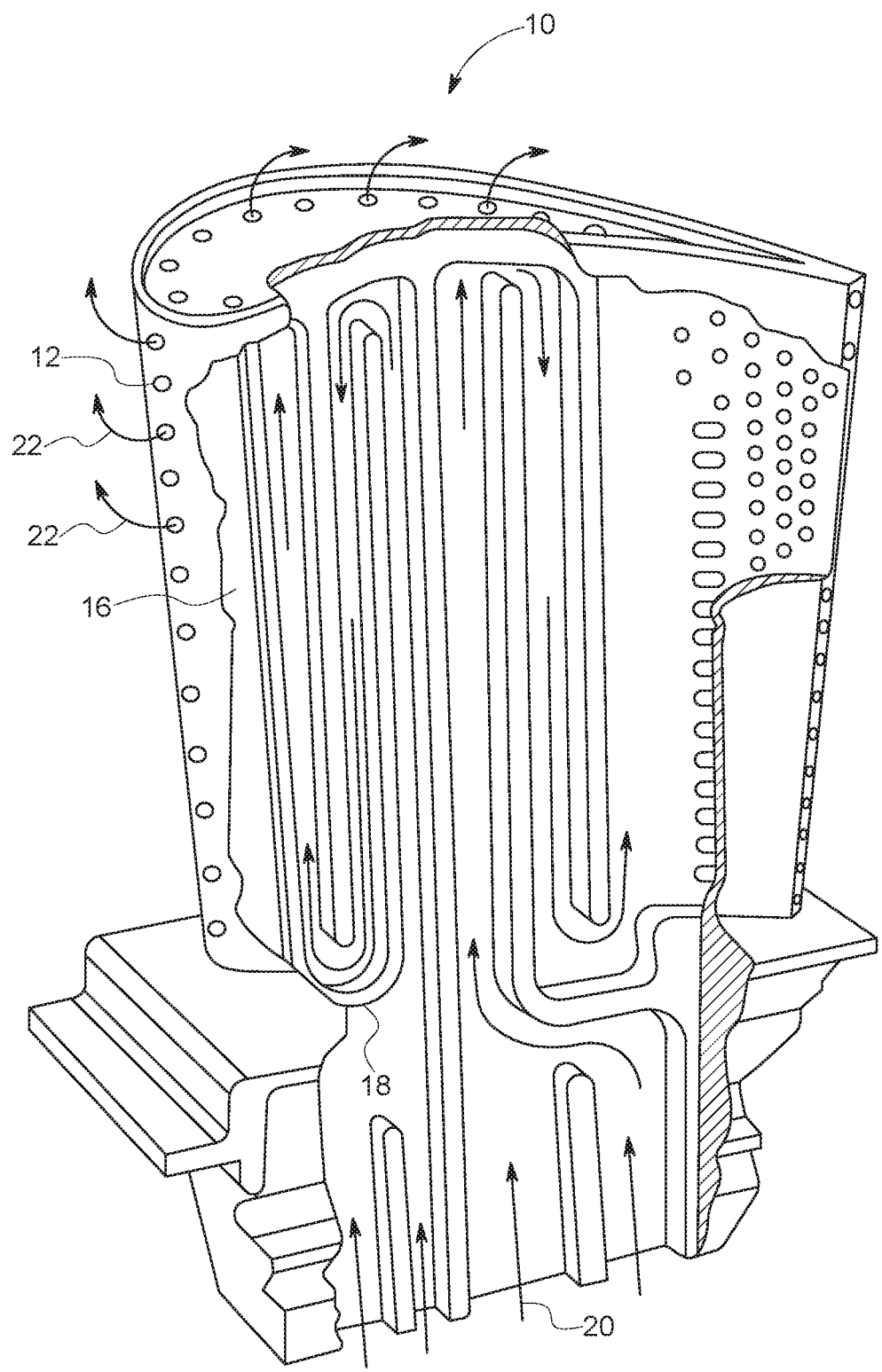
FIG. 1 illustrates a partial cutaway view of one example of a turbine engine blade.

FIG. 1 illustrates a partial cutaway view of one example of a turbine engine blade 10. The turbine blade 10 includes several cooling holes 12 formed in the blade 10. The cooling holes 12 fluidly couple a hollow interior or plenum 16 of the turbine blade 10. Fluid 20 flowing through the plenum 16 passes through interior baffles 18 of the turbine blade 10 and exits through the cooling holes 12 as exiting fluid 22. The fluid 20 may be a gas (such as air) that is at an elevated temperature. For example, the fluid 20 may be air that is warmer than an ambient temperature outside of the turbine blade 10. The fluid 20 may be above ambient temperature during inspection of the cooling holes 12, but may be less than the temperature to which the turbine blade 10 is exposed during operation of the turbine engine that includes the turbine blade 10. Alternatively, the fluid 20 may be a gas that is at or below the ambient temperature. The fluid 20 optionally may be a liquid, such as water.

Figure 2:
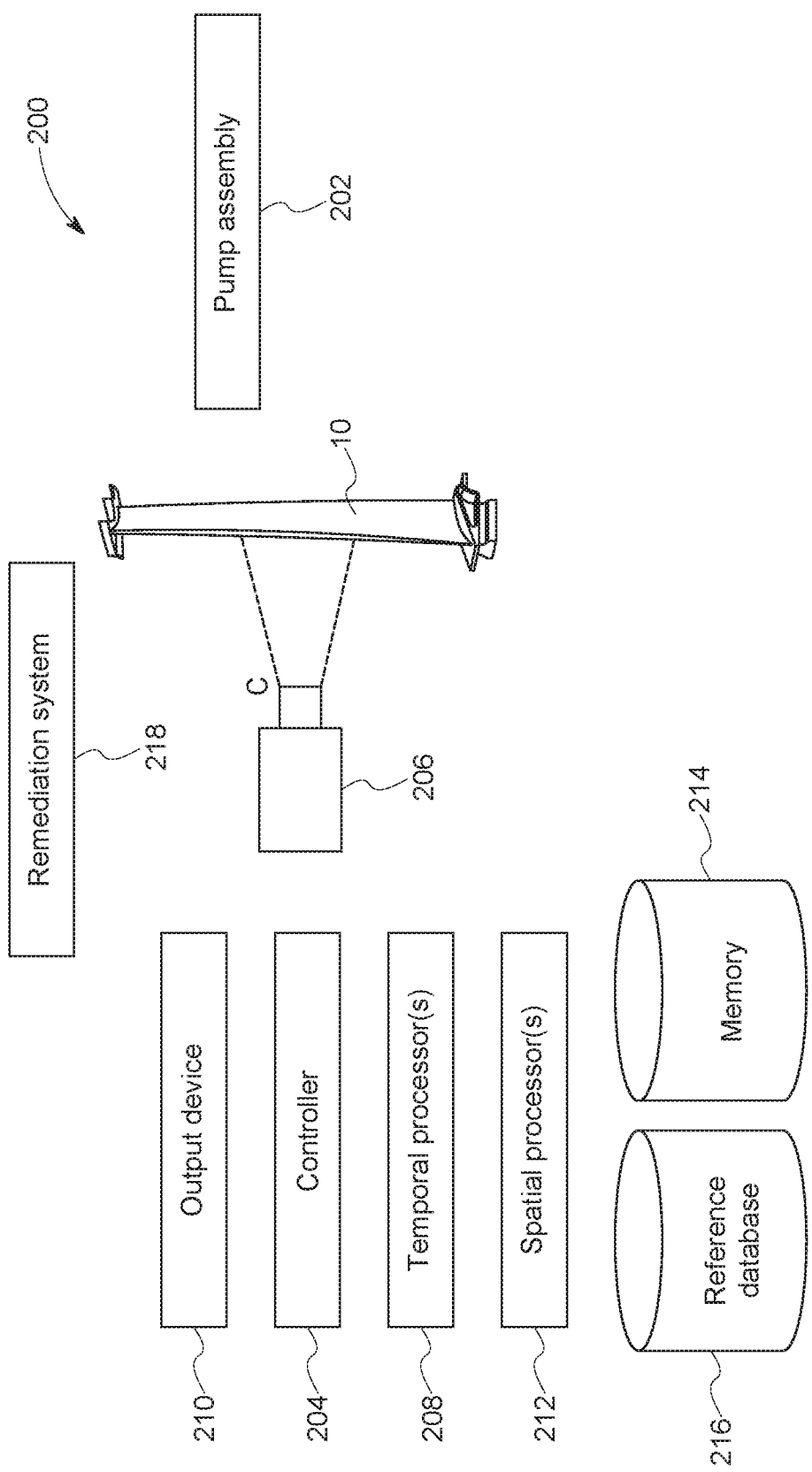
FIG. 2 illustrates one embodiment of a hole inspection system.

FIG. 2 illustrates one embodiment of a hole inspection system 200. The inspection system 200 can be used to examine the cooling holes 12 in components such as turbine blades 10 and to automatically identify the cooling hole 12 or holes 12 that are blocked or at least partially blocked. A cooling hole 12 may be blocked when no fluid 20 is able to flow through the cooling hole 12. For example, a cooling hole 12 may be blocked when the fluid 20 cannot flow from the plenum 16 to outside of the turbine blade 10 through the cooling hole 12. A cooling hole 12 may be partially blocked when some fluid 20 is able to pass through the cooling hole 12, but the outer perimeter of the cooling hole 12 is smaller or reduced relative to when the cooling hole 12 was first formed (e.g., due to clogging of the cooling hole 12 by the initial coating, or by sand, dirt, soot, or other contaminants). Optionally, the cooling hole 12 may be partially blocked when the cooling hole 12 is designed to be formed with a designated outer perimeter, but is actually formed with a smaller outer perimeter.

The inspection system 200 automatically identifies blocked or partially blocked cooling holes 12 by temporally processing thermographic data of the cooling holes 12, spatially processing the thermographic data of the cooling holes 12, and identifying the blocked or partially blocked cooling holes 12 based on outputs from the temporal and spatial processing of the thermographic data. The inspection system 200 independently processes the time domain of the thermographic data associated with each pixel (or other unit of data or display) in a video sequence of the thermographic data. This processing can collapse or otherwise reduce the thermographic data cube (of the changing pixel data over time) into a single normalized image having pixel values represent scores later used to identify the cooling holes 12 as blocked or not. The spatial processing of the thermographic data registers the thermographic data to find the location of the cooling holes 12, and calculates another score for the cooling hole 12 based on the spatial extent of the thermographic response of the cooling hole 12. The temporal and spatial scores are then combined into a composite score, which is examined to identify the cooling hole 12 as blocked, open, or partially blocked.

Figure 3:
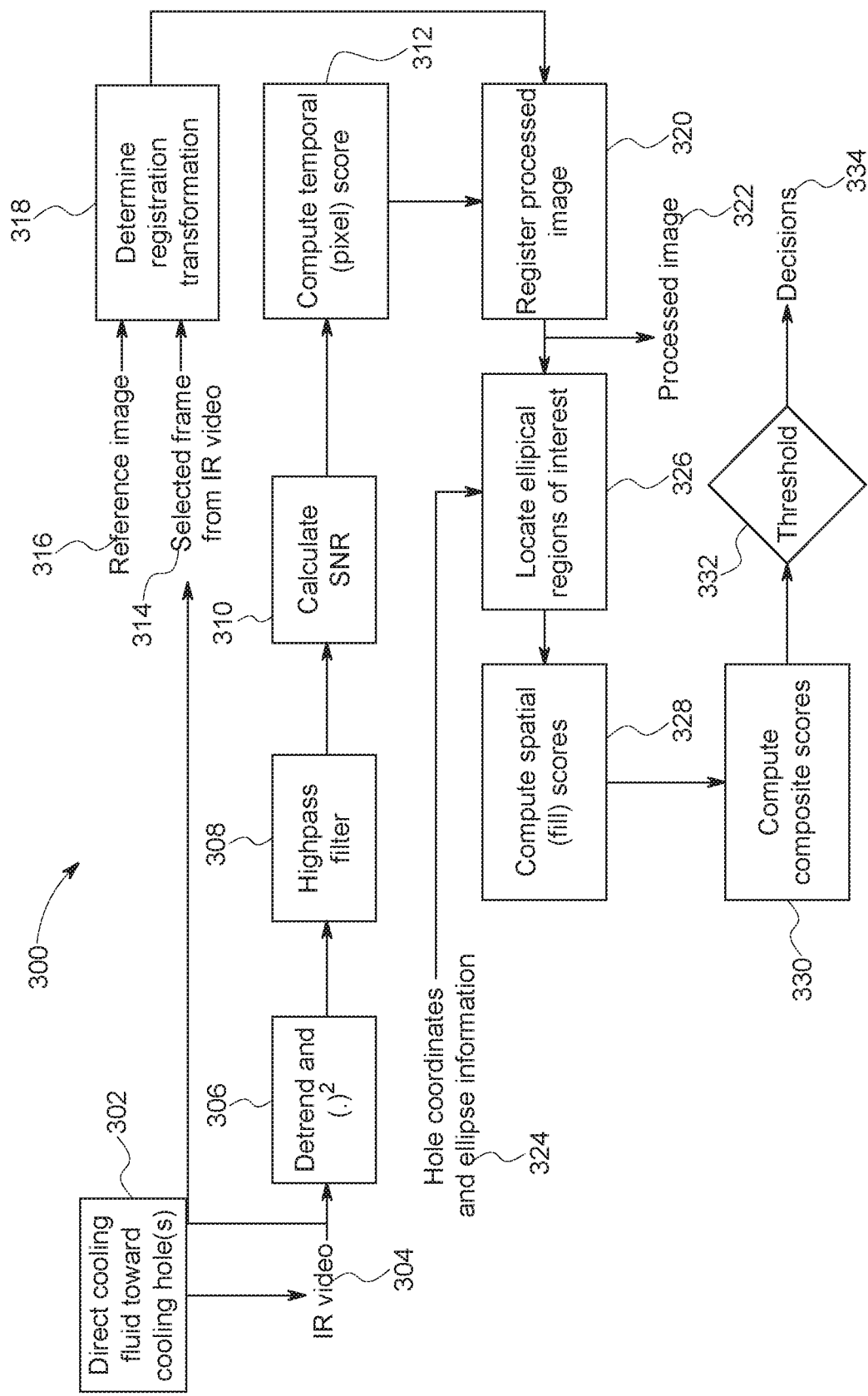
FIG. 3 illustrates a flowchart of one embodiment of a method for inspecting holes of a component.

With continued reference to the inspection system 200 shown in FIG. 2, FIG. 3 illustrates a flowchart of one embodiment of a method 300 for inspecting cooling holes of a component. The method 300 can represent the operations performed by various parts of the inspection system 200 to identify fully or partially blocked cooling holes 12, and optionally to implement one or more responsive actions after identifying a fully or partially blocked cooling hole 12. The operations described in connection with the method 300 can be performed in an order or sequence that differs from the illustrated and/or described sequence. For example, the temporal processing may be performed before, after, simultaneous with, or concurrently with, the spatial processing described herein.

The operations described in connection with the method 300 can be performed for each of several pixels (or other areas or volumes) of the thermographic data that is output from the thermographic sensor 206. For example, the calculations and scores that are determined in connection with the method 300 can be separately and independently performed for each pixel in the thermographic data output by the sensor 206, regardless of whether some pixels or areas do not represent temperatures of a cooling hole 12. Alternatively, the calculations and scores that are determined in connection with the method 300 can be separately and independently performed for each of the pixels in the thermographic data output by the sensor 206 that represent a cooling hole 12, and not performed for pixels that do not represent a cooling hole 12.

At 302, cooling fluid is directed toward cooling holes. The fluid 20 can be pumped or otherwise forced into the plenum 16 of the turbine blade 10 by a pump assembly 202 of the inspection system 200. The pump assembly 202 can include one or more pumps that are fluidly coupled with the plenum 16 by one or more conduits (not shown). The pump assembly 202 also can be coupled with a source of the fluid 20, such as an inlet and optional filters that collect ambient air for pumping into the plenum 16 as the fluid 20. Alternatively, the pump assembly 202 can be coupled with a tank or container of the fluid 20. The fluid 20 is forced into the plenum 16 by the pump assembly 202 and out of the open cooling holes 12 and/or partially out of the partially blocked cooling holes 12.

In one embodiment, the cooling fluid may be pulsed toward and/or through the cooling holes 12 being inspected. For example, the pump assembly 202 can repeatedly pump the fluid 20 into the plenum 16 and out of the open cooling holes 12 and/or partially out of the partially blocked cooling holes 12.

The rate at which the fluid 20 is pumped, the frequency at which the fluid 20 is pulsed, the amount of fluid 20 that is pumped, and the like, can be controlled by a controller 204 of the inspection system 200. The controller 204 includes hardware circuitry that includes and/or is connected with one or more processors (e.g., one or more microprocessors, one or more field programmable gate arrays, and/or one or more integrated circuits) that control operations described in connection with the controller 204.

In one embodiment, the pump assembly 202 directs compressed ambient air at a pressure of approximately three hundred pounds per square inch is pulsed through the plenum 16 of the blade 10 at a designated or operator-selected repetition rate and pulse duration. For example, between two hundred ninety pounds per square inch and three hundred ten pounds per square inch of air can be pumped into the plenum 16. The repetition rate indicates how rapidly the different pulses of air are directed into the plenum 16, and the pulse duration indicates how long air is directed into the plenum 16 for each pulse of air.

At 304 in the method 300, thermographic data of the cooling holes being inspected is obtained ("IR video" in FIG. 3). The controller 204 can direct a thermographic sensor 206, such as an infrared camera, to obtain the thermographic data. This thermographic data can include a video, static images, or a combination thereof, that indicates temperatures of the cooling holes 12 being inspected. The thermographic data can be saved in or on a tangible and non-transitory computer-readable storage medium, such as a computer memory 214. This memory 214 can represent one or more computer hard drives, optical discs, removable discs, or the like.

In one embodiment, an infrared camera is used as the thermographic sensor 206, and the camera captures a video sequence of the cooling holes 12 as the cooling fluid is pulsed toward the cooling holes 12. This video sequence can be obtained at one or more different frame rates, such as one hundred twenty frames per second, or the like. This thermographic data can represent temperature fluctuations of the areas in and/or around the cooling holes 12. The thermographic data can be a video sequence of these temperature fluctuations for several pulses of the fluid 20. The video sequence optionally can be referred to as a data cube, and can be provided to one or more temporal processors 208 of the inspection system 200.

The temporal processors 208 represent hardware circuitry that includes and/or is connected with one or more processors (e.g., one or more microprocessors, one or more field programmable gate arrays, and/or one or more integrated circuits) that perform the temporal processing of the thermographic data, as described herein. In one embodiment, the hardware circuitry and/or one or more of the processors of the controller 204 and the temporal processors 208 is the same hardware circuitry and/or the same processor. Alternatively, the controller 204 and temporal processors 208 may be separate circuits and/or processors.

Figure 4:
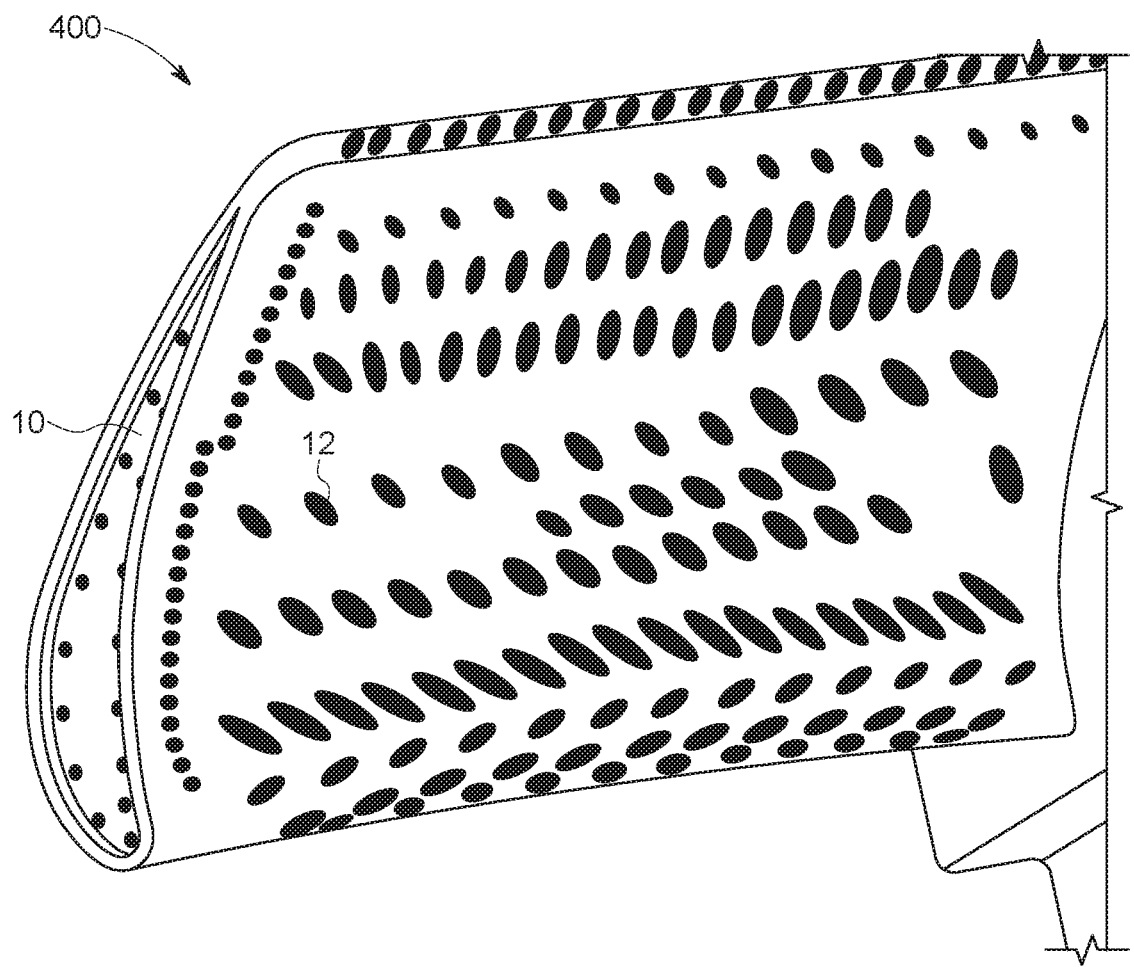
FIG. 4 illustrates one example frame of thermographic data obtained from a thermographic sensor.

FIG. 4 illustrates one example frame 400 of the thermographic data obtained from the thermographic sensor 206. The controller 204 can direct the thermographic sensor 206 to obtain video sequences at different orientations to the turbine blade 10. This can allow for the thermographic data to be obtained for each or all cooling holes 12 from a variety of different angles. Although not shown in FIG. 4, the controller 204 can generate and communicate control signals to motors, solenoids, or the like, that move the thermographic sensor 206 and/or the turbine blade 10 to obtain the thermographic data from the multiple different orientations.

Returning to the description of the flowchart of the method 300 shown in FIG. 3, one example of temporal processing of the thermographic video data is performed at 306, 308, and/or 312. The temporal processing can be performed by the temporal processors 208 and/or the controller 204. The temporal processing outputs temporal scores associated with different cooling holes 12 and/or different pixels in the thermographic video data. These temporal scores can be combined with spatial scores (described below) to determine whether a cooling hole 12 is at least partially blocked. A temporal score can be calculated for each pixel, for each pixel associated with a cooling hole 12, and/or for each cooling hole 12.

In one embodiment, the controller 204 can present one or more temporal scores, spatial scores, normalized images, thermographic data, other data signals, an identification of one or more cooling holes 12 being open, partially blocked, and/or fully blocked on an output device 210 of the inspection system 200. The output device 210 can represent an electronic display, speaker, or the like.

The temporal processor 208 can calculate a temporal score each pixel associated with a cooling hole 12 or for each cooling hole 12. The temporal scores can be stored in the memory 214.

Figure 5:
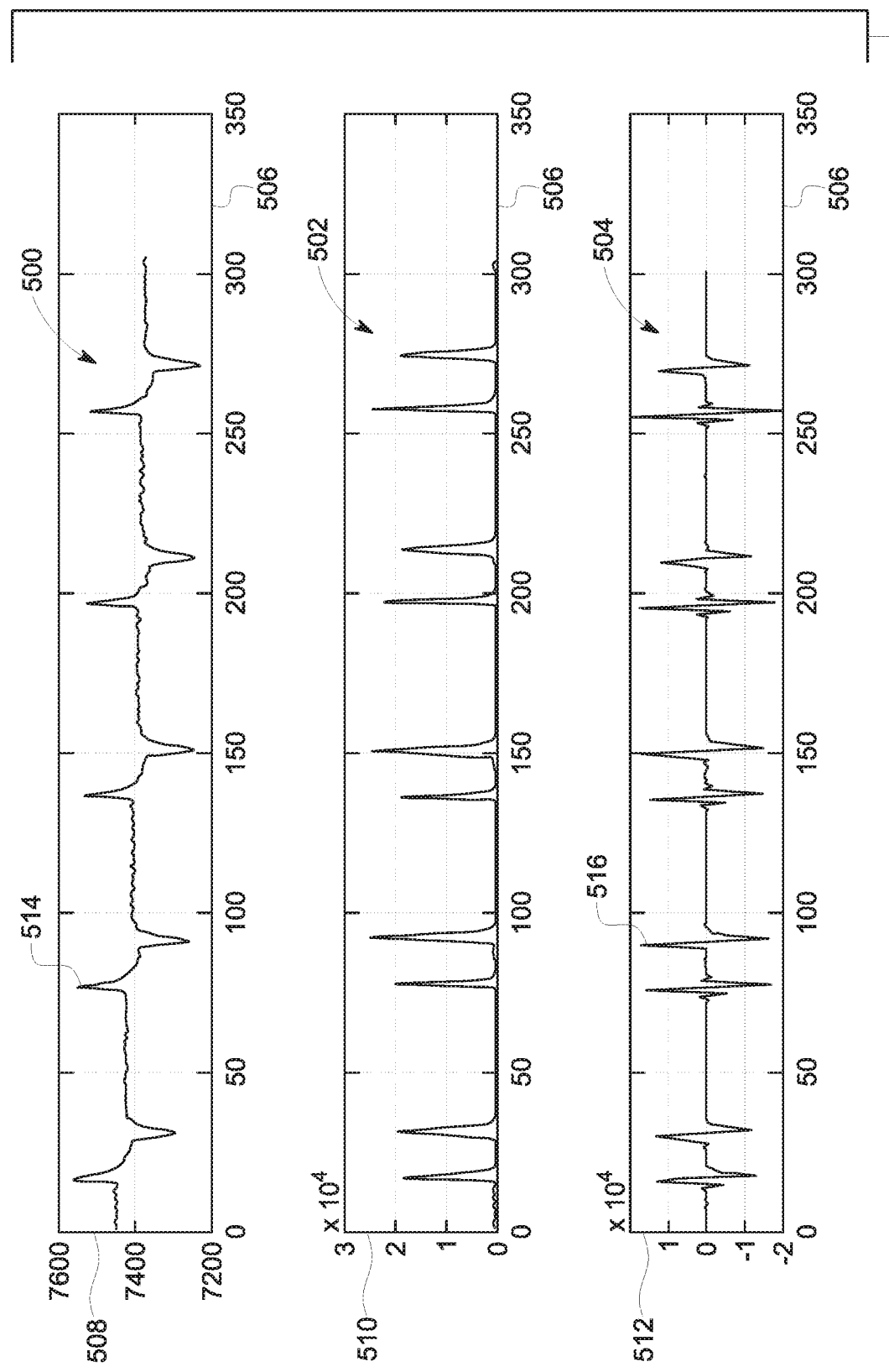
FIG. 5 illustrates a temporal thermographic data signal, a squared and detrended data signal, and a filtered data signal of a hole according to one example.

FIG. 5 illustrates a temporal thermographic data signal 500, a squared and detrended data signal 502, and a filtered data signal 504 of a cooling hole 12 according to one example. These data signals 500, 502, 504 can be stored in the memory 214. Each of the data signals 500, 502, 504 is shown alongside a horizontal axis 506 and a different vertical axis 508, 510, 512. The horizontal axis 506 represents time such that each of the data signals 500, 502, 504 is a time-domain signal. The temporal processor 208 can calculate or otherwise determine each of the data signals 500, 502, 504. As described above, the temporal processor 208 can calculate one or more of the signals 500, 502, 504 for individual pixels in the thermographic data that is output by the thermographic sensor 206. For example, the data signals 500, 502, and/or 504 can be calculated for each pixel that is in the thermographic data, regardless of whether a pixel represents a cooling hole 12. Alternatively, the data signals 500, 502, and/or 504 can be calculated for each pixel that represents a location of a cooling hole 12 in the thermographic data, and not for pixels that do not represent a location of a cooling hole 12.

The temporal thermographic data signal 500 represents the temperatures measured or represented by the thermographic video signal output by the thermographic sensor 206. For example, the temporal thermographic data signal 500 can represent the magnitude of temperature or brightness of a pixel in the thermographic video associated with a cooling hole 12 being examined. As shown, the magnitude of the temporal thermographic data signal 500 periodically increases and then decreases, indicating a regular change in temperature at or near the cooling hole 12. The temporal thermographic data signal 500 can periodically change at a rate or frequency that corresponds with the rate or frequency at which pulses of the fluid 20 are directed toward the cooling hole 12. For example, the temporal thermographic data signal 500 can change at a rate or frequency that is the same as the rate or frequency at which the pulses of fluid 20 are directed toward the cooling hole 12. Peaks 514 in the temporal thermographic data signal 500 can correspond to onset (e.g., the beginning) of each pulse of the fluid 20.

In one embodiment of the method 300, at 306, the detrended and squared data signal is determined. For example, at 306, a downward linear trend in the data signal 500 is determined and removed from the data signal 500, and squared values of the detrended data signal 500 are calculated. The temporal processor 208 can calculate the detrended and squared data signal 502 by determining a downward linear trend across the data signal 500, and removing the downward linear trend from the data signal 500, and squaring the values of the detrended data signal 500. The linear trend may be drift in the thermographic data signal 500 over time caused by repeated heating or cooling of the turbine blade 10 by the repeated pulses of fluid 20. The linear trend can be calculated by fitting a straight line to the data signal 500, such as the values of the data signal 500 between the peaks 514, the values of the data signal 500 including the peaks 514, or the values of the data signal 500 that are not squared. Optionally, the linear trend may not be identified or removed from the data signal 500.

The temporal processor 208 can then calculate the filtered signal 504 by applying a highpass filter to the signal 502. The filtered signal 504 can approximate the high frequency variations of the detrended and squared data signal 502.

The filtered signal 504 also includes several steeper peaks 516 that correspond with the peaks 514 in the temporal thermographic signal 500. The peaks 514, 516 in the data signals 500, 504 are located between increasing portions and decreasing portions of the data signals 500, 504.

At 310, a signal-to-noise ratio is calculated for the signal 504. The temporal processor 208 can calculate the temporal score for the pixel based on the signal 504. For example, the temporal processor 208 can calculate a signal-to-noise ratio of the signal 504 as the temporal score.

Figure 6:
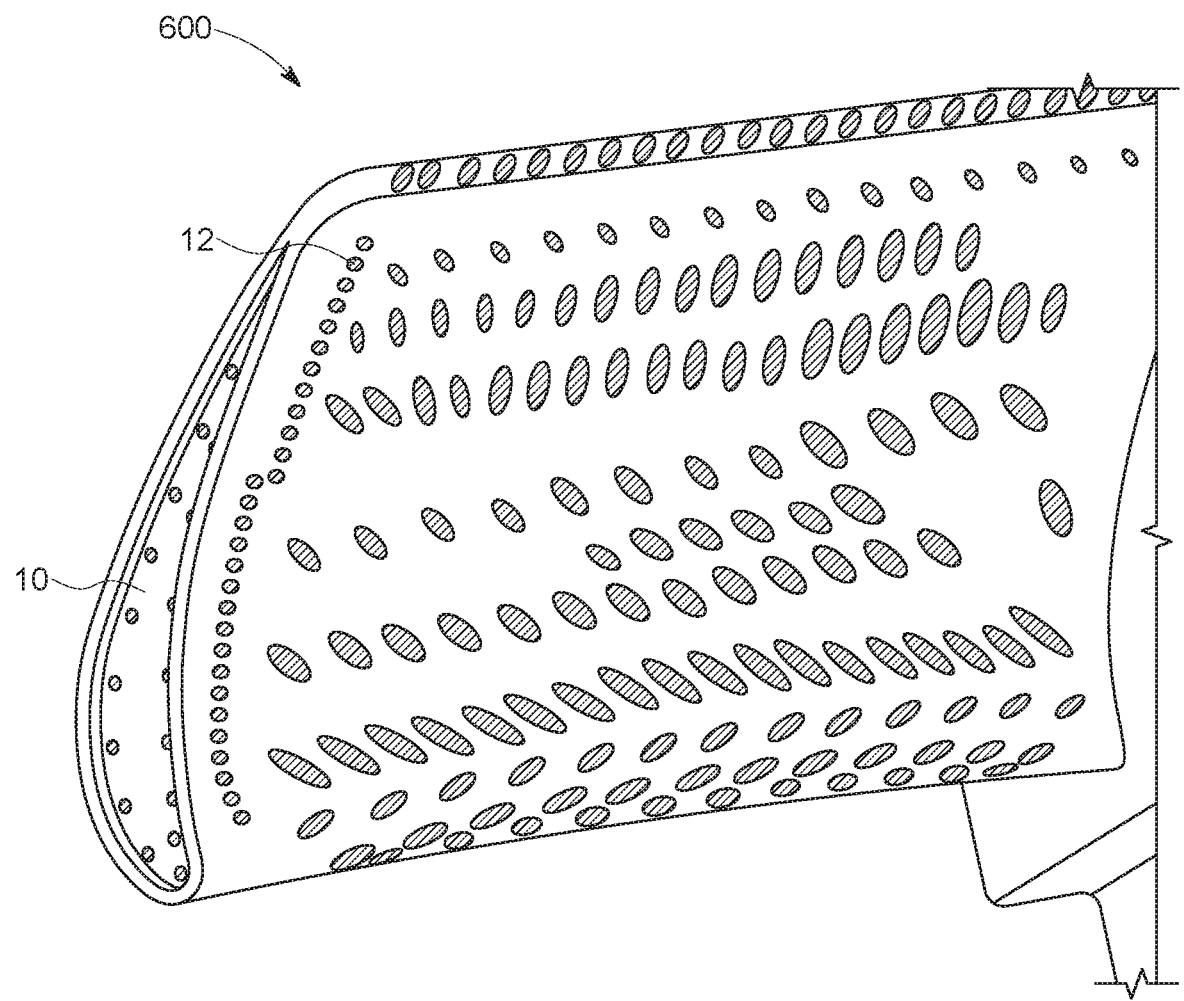
FIG. 6 shows a normalized image for a portion of the blade shown in FIG. 1.

In one embodiment, the temporal processor 208 can create a normalized image of the blade 10 using the temporal scores for the pixels. The normalized image can be stored in the memory 214. FIG. 6 shows a normalized image 600 for a portion of the blade 10. The normalized image 600 can be formed by the temporal processor 208 changing how a pixel is displayed on the output device 210 based on the temporal score of the pixel. For example, larger temporal scores (e.g., closer to one than zero) may be displayed as white or close to white pixels, while smaller temporal scores (e.g., closer to zero than one) may be displayed as black or close to black pixels. As shown, the pixels representative of cooling holes 12 have different temporal scores than the pixels representative of the remainder of the blade 10. Because the temporal signal for each pixel is separately analyzed by the temporal processor 208, the normalized image 600 represents the independent processing of the time domain thermographic signals for the pixels.

Returning to the description of the flowchart of the method 300 shown in FIG. 3, the method 300 can include (at 314, 316, 318, 320, 322, 324, 326, and/or 328) spatial processing of the thermographic data that is output by the thermographic sensor 206. This spatial processing can be performed to determine one or more spatial scores for one or more cooling holes, and the temporal score and the spatial score associated with the same cooling hole can be examined (as described below) to determine whether the cooling hole is open, blocked or partially blocked. Alternatively, the method 300 may use the temporal scores, and not the spatial scores, to determine whether any cooling holes are blocked or partially blocked.

At 314, a frame from the video output by the thermographic sensor is selected. One or more spatial processors 212 of the system 200 represent hardware circuitry that includes and/or is connected with one or more processors (e.g., one or more microprocessors, one or more field programmable gate arrays, and/or one or more integrated circuits) that perform the spatial processing of the thermographic data, as described herein. In one embodiment, the hardware circuitry and/or one or more of the processors of the controller 204, the temporal processor 208, and/or the spatial processor 212 is the same hardware circuitry and/or the same processor. Alternatively, the controller 204, the temporal processor 208, and/or the spatial processor 212 may be separate circuits and/or processors.

The spatial processor 212 can select the frame from the thermographic data output from the thermographic sensor 206. For example, the spatial processor 212 can select the same frame that corresponds with the normalized image determined by the temporal processor 208. Optionally, the spatial processor 212 can select another image frame.

At 316, a reference image is obtained. Several reference images can be stored in the memory 214 or in another tangible and non-transitory computer readable medium, such as another computer memory 216 ("Reference Database" in FIG. 2) of the system 200. The reference image can be selected by the spatial processor 212 from among several different reference images. The different reference images may represent the locations of cooling holes 12 in the blade 10 at different orientations and/or locations. The orientation and/or location at which the thermographic data is obtained by the sensor 206 can be provided to the spatial processor 212 (e.g., by the sensor 206 and/or operator input), and the spatial processor 212 can examine the reference images to determine which reference image has the same or most similar orientation and/or location. For example, metadata or other data associated with the different reference images can indicate the locations on the blade 10 depicted in the reference images and/or the orientations at which the reference images were obtained. The spatial processor 212 can examine this metadata or other data to determine which reference image depicts the same or similar location and/or orientation of the blade 10. A reference image with the similar location and/or orientation can be the reference image depicting a location and/or orientation that is closer to the location and/or orientation imaged by the sensor 206 than one or more (or all) other reference images.

The reference image optionally can include or be stored with location data indicating where the cooling holes 12 are located within the reference image. This location data can be stored with the reference image in the memory 216. For example, the reference images can be stored with coordinates, pixel locations, or the like, that indicate where the cooling holes 12 are shown in the reference images.

At 318, a registration transformation of the selected thermographic frame is determined. The spatial processor 212 can determine how the selected thermographic frame and/or the registration image need to be rotated and/or linearly moved so that the thermographic frame selected at 314 and the reference image obtained at 316 are aligned. The spatial processor 212 can determine a transformation of the frame and/or image as a rotation and/or linear movement of the frame and/or image to align the frame and image for best matching of the cooling holes 12 in the frame and image. The transformation can be a three by three matrix having a two by two rotation matrix and two additional numbers specifying linear movements in orthogonal directions (e.g., along perpendicular x- and y-directions).

At 320, the thermographic video frame and/or the reference image are registered to each other. The spatial processor 212 can apply the transformation to the frame and/or to the image to produce a processed, registered image having a known or designated alignment. The spatial processor 212 can then determine where the cooling holes 12 are located (or should be located) in the thermographic video frame based on the known locations of the cooling holes 12 in the reference image. Because the frame and image have the same alignment, the spatial processor 212 can use the known locations of the cooling holes 12 in the reference image to determine where the cooling holes 12 are or should be located in the video frame.

Optionally, a cooling hole refinement process can be performed. This refinement process can be performed by the spatial processor 212 to determine the locations of at least some of the cooling holes 12 in the thermographic video frame. The relative locations of the cooling holes 12 may be known (e.g., stored in the memory 214 and/or 216), such as from the manufacturing specifications of the blade 10. For example, vectors defining the distance and angle from one cooling hole 12 to another (e.g., neighboring) cooling hole 12 may be stored in the memory 214 and/or 216.

The spatial processor 212 can examine the thermographic video frame and compare intensities (or colors or other features) of the pixels in the frame to identify one or more cooling holes 12. For example, a cooling hole 12 may appear brighter or in a different color in the frame than other parts of the blade 10 that are not cooling holes 12. The spatial processor 212 can use the different appearance of the cooling holes 12 to automatically find at least one cooling hole 12. The spatial processor 212 can then record the location of the found cooling hole 12 in the memory 214 and/or 216.

The spatial processor 212 can then examine the frame in areas from the found cooling hole 12 where another cooling hole 12 should be located (based on the known relative locations of the cooling holes 12). For example, if the cooling holes are designed to be a designated distance away from each other, the spatial processor 212 can examine the frame in several potential locations that are the designated distance away from the location of the found cooling hole 12. The spatial processor 212 can examine these potential locations to determine whether the pixels at these potential locations indicate that a cooling hole 12 is at one or more of the potential locations (e.g., using the characteristics of the pixels, such as the intensities, colors, etc.). Once the additional cooling hole 12 is found, the spatial processor 212 can repeat this sequential, iterative process to find the locations of additional cooling holes 12 in the frame.

In one embodiment, at 322, the frame having the identified locations of the cooling holes 12 is output as a processed image. The spatial processor 212 can send the frame with the identified cooling hole locations to the memory 214, 216 and/or to the output device 210 as the processed image. This can permit an operator of the system 200 to view the processed image to verify or otherwise inspect the cooling holes 12 identified by the spatial processor 212.

At 324, the hole locations and cooling hole shape information are obtained. The hole locations are referred to as "hole coordinates" and the cooling hole shape information is referred to as "ellipse information" in FIG. 3. The cooling hole locations can be determined at 320, as described above. The shape information is information indicating the shape of the cooling holes 12. Some cooling holes 12 may have an elliptical shape, while other cooling holes 12 can have other shapes (e.g., circles, polygons, etc.). The shapes of the cooling holes 12 can be stored in the memory 216 and can be retrieved from the memory 216 by the spatial processor 212. The shape information of the cooling holes 12 assists the spatial processor 212 in examining a designated set of pixels in the registered thermographic video frame that are associated with a cooling hole 12 to determine the spatial score for that cooling hole 12.

The shapes associated with the cooling holes 12 can be based on the identified locations of the cooling holes 12. For example, the cooling holes 12 in different areas of the turbine blade 10 can have different shapes. The cooling holes 12 near one or more edges of the blade 10 may have one shape, while the cooling holes 12 farther from the edges of the blade 10 may have another, different shape. The spatial processor 212 can examine the identified locations of the cooling holes 12 in the registered frame and determine the designated shapes of these cooling holes 12 based on the identified locations.

At 326, areas (or regions) of interest around the cooling holes are identified. The spatial processor 212 can identify areas of interest around the cooling holes 12 based on the designated shapes associated with the cooling holes 12. While FIG. 3 refers to the areas of interest as "elliptical regions of interest," not all embodiments of the inventive subject matter are limited to elliptical regions of interest. As described above, the regions or shapes may have another non-elliptical shape, such as a circle, polygon, or the like. The region of interest for a cooling hole 12 includes the area around the identified location of the cooling hole 12 that is within the designated shape associated with the cooling hole 12. For example, the spatial processor 212 can select those pixels that are within the elliptical shape of a cooling hole 12 (around the identified location of the cooling hole 12) in the registered frame as the region of interest for that cooling hole 12. The spatial processor 212 can position the designated shape of the cooling hole 12 around the cooling hole 12 so that the cooling hole 12 is at a center of the designated shape or at another location. For example, the spatial processor 212 can position a designated elliptical shape around the cooling hole 12 with the identified location of the cooling hole 12 at one of the focal points of the elliptical shape. As another example, the spatial processor 212 can position a designated shape around the cooling hole 12 with the identified location of the cooling hole 12 at the center of the shape. Optionally, the spatial processor 212 can position a designated shape around the cooling hole 12 with the identified location of the cooling hole 12 being on an outer edge of the designated shape.

The spatial processor 212 also can orient the designated shapes with respect to the cooling holes 12. For example, different cooling holes 12 may be oriented different direction based on where the cooling holes 12 are located in the blade 10. Cooling holes 12 in one area of the blade 10 may have elliptical shapes with the focal points of the elliptical shapes located along first lines, while the cooling holes 12 in another area of the blade 10 may have elliptical shapes with the focal points of the elliptical shapes located along different, second lines, where the first and second lines are at different angles with respect to each other and/or a center axis of the blade 10. The orientations of the designated shapes of the cooling holes 12 can be stored in the memory 216 and obtained by the spatial processor 212.

Figure 7:
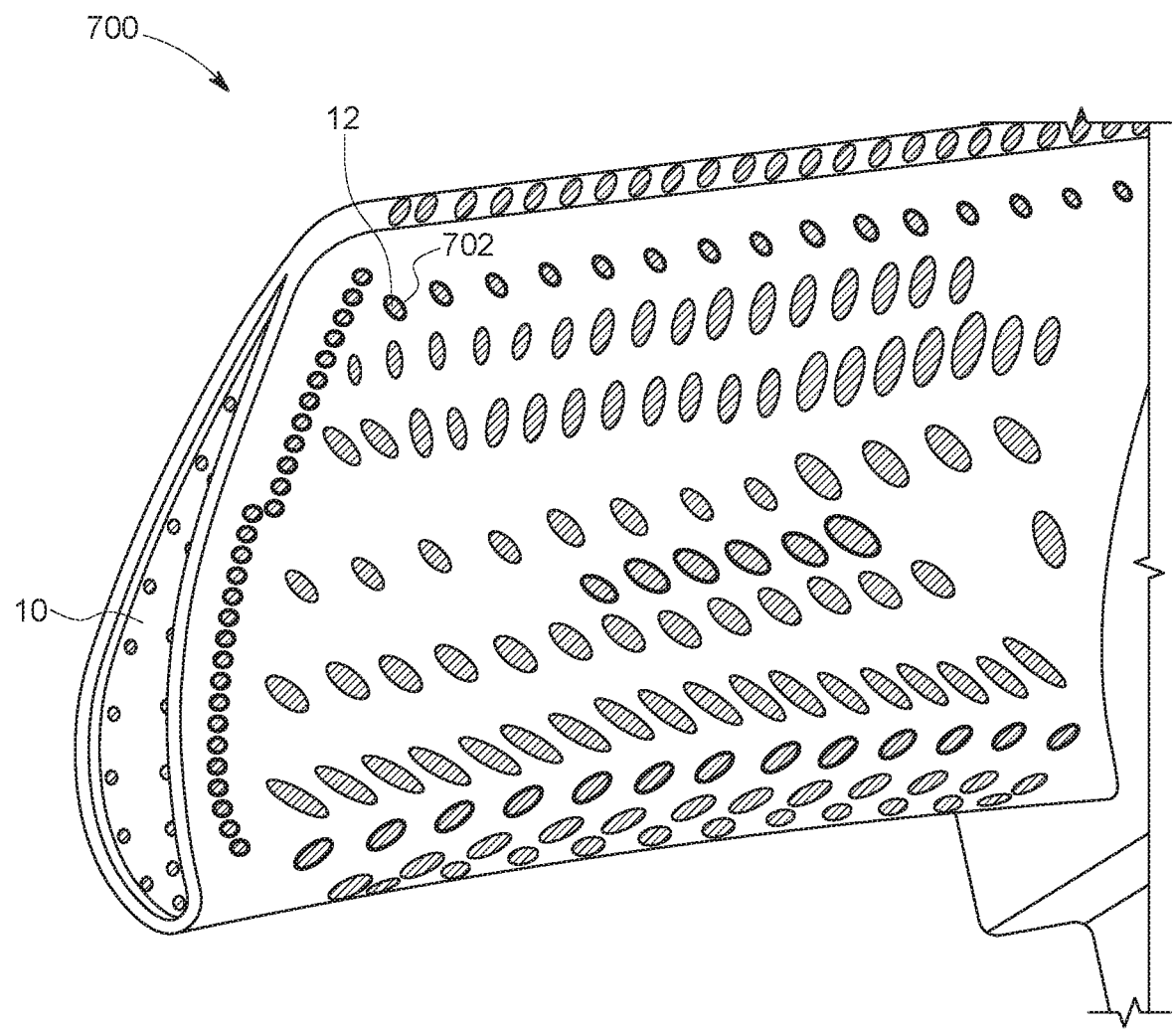
FIG. 7 illustrates a registered frame for a portion of the blade shown in FIG. 1.

FIG. 7 illustrates a registered frame 700 for a portion of the blade 10. The registered frame 700 can be the registered frame obtained from or based on the normalized image 600 shown in FIG. 6. The frame 700 shows a portion of the blade 10 and several cooling holes 12. Several identified regions of interest 702 around the cooling holes 12 also are shown in FIG. 7. The regions of interest 702 are the areas around the cooling holes 12 that are identified by the spatial processor 212, as described above. The spatial processor 212 can include the pixels in the frame 700 that are within the regions of interest 702 to be associated with the corresponding cooling hole 12. For example, the spatial processor 212 can associate the pixels within the region of interest 702 of a cooling hole 12 with that cooling hole. As a result, different cooling holes 12 in the frame 700 are associated with different groups of pixels. In one embodiment, the cooling holes 12 are located and the designated shapes are sized and oriented such that no pixel in the frame 700 is included in regions of interest 702 associated with different cooling holes 12.

Returning to the description of the flowchart of the method 300 shown in FIG. 3, at 328, spatial scores are determined for the cooling holes. The spatial processor 212 can calculate the spatial scores for the cooling holes 12 based on characteristics of the pixels associated with the different cooling holes 12. As one example, the spatial processor 212 can calculate the spatial score for a cooling hole 12 as the fraction of pixels within the region of interest 702 of that cooling hole 12 that have a characteristic that exceeds a designated lower limit. This characteristic can be an intensity, contrast, or the like, of the pixels. Alternatively, this characteristic can be the temporal score of the pixel, as described above. The lower limit can be a default system limit and/or a limit that can be modified by an operator of the system 200.

At 330, a composite score for one or more cooling holes is calculated. The spatial processor 212 can calculate a composite score for each of two or more cooling holes 12 (but not necessarily all cooling holes 12) based on both the temporal score and the spatial score for the cooling hole 12. In one embodiment, the composite score for a cooling hole 12 is an average of the spatial score of the region of interest 702 of the cooling hole 12 and a median of a designated portion of the temporal scores for those pixels within the region of interest 702 of the cooling hole 12. The inventors of this subject matter have discovered that this calculation of the composite score for a cooling hole 12 provides an unexpectedly accurate identification of whether the cooling hole 12 is open, blocked, or partially blocked relative to other calculations.

Alternatively, the composite score can be calculated in another manner. For example, the composite score can be an addition of the temporal score and the spatial score for the cooling hole 12. As another example, the composite score for a cooling hole 12 can be the temporal score added to the spatial score. Alternatively, the composite score can be a product of the temporal score and the spatial score, can be an addition of the temporal score and the spatial score with at least one of these scores being weighted differently than the other score, can be a division of the temporal score by the spatial score, can be a division of the spatial score by the temporal score, or the like. The composite scores can be calculated by the spatial processor 212 and stored in the memory 214 and/or presented on the output device 210.

At 332, the composite scores of the cooling holes are examined to determine whether the cooling holes are open, blocked or partially blocked. The spatial processor 212 can compare the composite scores to one or more designated limits and identify cooling holes 12 as open, blocked or partially blocked based on this comparison. For example, larger composite scores (e.g., those that exceed the limit) can be identified by the spatial processor 212 as being open, while smaller composite scores (e.g., those that do not exceed the limit) being identified by the spatial processor 212 as being blocked.

At 334, decisions are made as to whether cooling holes are open or blocked based on the comparison performed at 332. The spatial processor 212 can record which cooling holes 12 are open and/or which cooling holes 12 are blocked in the memory 214. The spatial processor 212 optionally can present information to an operator on which cooling holes 12 are open and/or which cooling holes 12 are blocked on the output device 210.

In one embodiment, one or more responsive actions can be performed based on the decision on whether cooling holes 12 are blocked. For example, responsive to determining that cooling holes 12 are blocked, the controller 204 can communicate a signal to a remediation system 218 that automatically operates to unblock or otherwise clear the blocked cooling holes 12, such as by removing blocking bodies in the cooling holes 12 that are blocking the cooling holes 12. The remediation system 218 can be an automated cleaning system, such as a sand blasting system, a water (or other fluid) washing system, or the like, that directs cleaning materials (e.g., sand, water, detergent, or the like) toward the blocked cooling holes 12 to open these cooling holes 12. Alternatively, one or more other responsive actions can be implemented, such as the controller 204 automatically scheduling the blade 10 for further inspection, machining, and/or cleaning, automatically modifying a schedule of a vehicle or powered system that includes the blade 10 so that the vehicle or powered system no longer operates due to the blocked cooling holes 12, automatically restricting operation of the vehicle or powered system that includes the blade 10 so that the vehicle or powered system is not allowed to operate above a designated limit due to the blocked cooling holes 12, or the like.

While the inventive subject matter has been described with regard to the inspection of cooling holes of a gas turbine engine blade, the inventive subject matter may be used to detect defects in any type of hole or channel formed through a workpiece. The inventive subject matter is not limited to the specific embodiments described and illustrated herein. Different embodiments and adaptations besides those shown herein and described, as well as many variations, modifications and equivalent arrangements will now be apparent or will be reasonably suggested by the foregoing specification and drawings, without departing from the substance or scope of the inventive subject matter. While the inventive subject matter has been described herein in detail in addition to its preferred embodiment, it is to be understood that this disclosure is only illustrative and an example of the inventive subject matter and is made merely for purposes of providing a full and enabling disclosure of the inventive subject matter.

In one embodiment, a method for detecting blockage of holes in a component is provided. The method includes capturing thermographic data of the component and the holes as a fluid is pulsed toward the holes, temporally processing the thermographic data to calculate temporal scores for the corresponding holes, spatially processing the thermographic data to calculate spatial scores for the corresponding holes, and calculating composite scores associated with the holes based on the temporal scores and based on the spatial scores. The composite scores represent a likelihood that the corresponding holes are open, blocked, or partially.

Optionally, the component is a turbine blade and the holes are cooling holes through which a cooling fluid flows to cool the turbine blade during operation of the turbine blade.

Optionally, the fluid is pulsed toward the holes on a repeated periodic basis.

Optionally, the method also includes creating a normalized image of the holes based on temporally processing the thermographic data.

Optionally, the temporal score is calculated for each of several pixels associated with the holes.

Optionally, the temporal scores are calculated for the holes based on a signal to noise ratio of the thermographic data.

Optionally, the temporal scores are calculated for the holes based on detrended values of the thermographic data.

Optionally, the temporal scores are calculated for the holes based on squared values of the detrended thermographic data.

Optionally, temporally processing the thermographic data includes detrending and squaring time domain signals of the thermographic data for the holes, applying a highpass filter to the thermographic data that is detrended and squared, and calculating a signal to noise ratio of the thermographic data after the highpass filter is applied.

Optionally, the spatial scores are calculated based on a fraction of pixels in the thermographic data associated with each of the holes having at least a designated temperature response within a designated area around the hole.

Optionally, the composite score for each of the holes is calculated as one or more of: an average or a median of the spatial score for the hole and one or more an average or median of a portion of the temporal scores for the hole.

Optionally, the composite score for each of the holes is compared with a designated threshold for the hole to determine whether the hole is open, blocked, or partially blocked.

Optionally, the method also includes opening one or more of the holes that is determined to be blocked or partially blocked.

Optionally, the method also includes obtaining a thermographic frame from the thermographic data, obtaining a reference image representative of hole locations in the component or another component, aligning the thermographic frame with the reference image by spatially transforming an orientation of the thermographic frame to match an orientation of the reference image, and identifying locations of the holes in the component using the thermographic frame that has been spatially transformed.

In one embodiment, an inspection system includes a thermographic sensor configured to capture thermographic data of a component having holes as a fluid is pulsed toward the holes, and one or more processors configured to temporally process the thermographic data to calculate temporal scores for the corresponding holes, spatially process the thermographic data to calculate spatial scores for the corresponding holes, and calculate composite scores associated with the holes based on the temporal scores and based on the spatial scores. The composite scores represent a likelihood that the corresponding holes are open, blocked, or partially blocked.

Optionally, the one or more processors are configured to calculate the temporal scores for the holes based on a signal to noise ratio of the thermographic data.

Optionally, the one or more processors are configured to calculate the spatial scores based on a fraction of pixels in the thermographic data associated with each of the holes having at least a designated temperature response within a designated area around the hole.

In one embodiment, a method for detecting blockage of cooling holes in a turbine blade is provided. The method includes capturing thermographic data of the turbine blade and the cooling holes as a fluid is pulsed toward the cooling holes, temporally processing the thermographic data to calculate temporal scores for the corresponding cooling holes, spatially processing the thermographic data to calculate spatial scores for the corresponding cooling holes, and calculating composite scores associated with the cooling holes based on the temporal scores and based on the spatial scores. The composite scores represent a likelihood that the corresponding cooling holes are blocked.

Optionally, temporally processing the thermographic data includes detrending and squaring time domain signals of the thermographic data for the cooling holes, applying a highpass filter to the thermographic data that has been detrended and squared, and calculating a signal to noise ratio of the thermographic data that has been detrended and squared and after the highpass filter is applied.

Optionally, the spatial scores are calculated based on a fraction of pixels in the thermographic data associated with each of the cooling holes having at least a designated temperature response within a designated area around the cooling hole.

Optionally, the method also includes opening one or more of the cooling holes that is determined to be blocked or partially blocked.

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the subject matter set forth herein, including the best mode, and also to enable a person of ordinary skill in the art to practice the embodiments of disclosed subject matter, including making and using the devices or systems and performing the methods. The patentable scope of the subject matter described herein is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A method for detecting blockage of holes in a component, the method comprising:
    capturing thermographic data of the component and the holes as a fluid is pulsed toward the holes;
    temporally processing the thermographic data to calculate temporal scores for the corresponding holes;
    spatially processing the thermographic data to calculate spatial scores for the corresponding holes; and
    calculating composite scores associated with the holes based on the temporal scores and based on the spatial scores,
    wherein the composite scores represent a likelihood that the corresponding holes are open, blocked, or partially blocked.

2. The method of claim 1, wherein the component is a turbine blade and the holes are cooling holes through which a cooling fluid flows to cool the turbine blade during operation of the turbine blade.

3. The method of claim 1, wherein the fluid is pulsed toward the holes on a repeated periodic basis.

4. The method of claim 1, further comprising:
    creating a normalized image of the holes based on temporally processing the thermographic data.

5. The method of claim 1, wherein the temporal score is calculated for each of several pixels associated with the holes.

6. The method of claim 1, wherein the temporal scores are calculated for the holes based on a signal to noise ratio of the thermographic data.

7. The method of claim 1, wherein the temporal scores are calculated for the holes based on detrended values of the thermographic data.

8. The method of claim 1, wherein the temporal scores are calculated for the holes based on squared values of the detrended thermographic data.

9. The method of claim 1, wherein temporally processing the thermographic data includes:
    detrending and squaring time domain signals of the thermographic data for the holes;

applying a highpass filter to the thermographic data that is detrended and squared; and calculating a signal to noise ratio of the thermographic data after the highpass filter is applied.

10. The method of claim 1, wherein the spatial scores are calculated based on a fraction of pixels in the thermographic data associated with each of the holes having at least a designated temperature response within a designated area around the hole.

11. The method of claim 1, wherein the composite score for each of the holes is calculated as one or more of: an average or a median of the spatial score for the hole and one or more an average or median of a portion of the temporal scores for the hole.

12. The method of claim 1, wherein the composite score for each of the holes is compared with a designated threshold for the hole to determine whether the hole is open, blocked, or partially blocked.

13. The method of claim 1, further comprising opening one or more of the holes that is determined to be blocked or partially blocked.

14. The method of claim 1, further comprising:
obtaining a thermographic frame from the thermographic data;
obtaining a reference image representative of hole locations in the component or another component;
aligning the thermographic frame with the reference image by spatially transforming an orientation of the thermographic frame to match an orientation of the reference image; and
identifying locations of the holes in the component using the thermographic frame that has been spatially transformed.

15. An inspection system comprising:
a thermographic sensor configured to capture thermographic data of a component having holes as a fluid is pulsed toward the holes; and
one or more processors configured to temporally process the thermographic data to calculate temporal scores for the corresponding holes, spatially process the thermographic data to calculate spatial scores for the corresponding holes, and calculate composite scores associated with the holes based on the temporal scores and based on the spatial scores,
wherein the composite scores represent a likelihood that the corresponding holes are open, blocked, or partially blocked.

16. The system of claim 15, wherein the one or more processors are configured to calculate the temporal scores for the holes based on a signal to noise ratio of the thermographic data.

17. The system of claim 15, wherein the one or more processors are configured to calculate the spatial scores based on a fraction of pixels in the thermographic data associated with each of the holes having at least a designated temperature response within a designated area around the hole.

18. A method for detecting blockage of cooling holes in a turbine blade, the method comprising:
capturing thermographic data of the turbine blade and the cooling holes as a fluid is pulsed toward the cooling holes;
temporally processing the thermographic data to calculate temporal scores for the corresponding cooling holes;
spatially processing the thermographic data to calculate spatial scores for the corresponding cooling holes; and
calculating composite scores associated with the cooling holes based on the temporal scores and based on the spatial scores,
wherein the composite scores represent a likelihood that the corresponding cooling holes are open, blocked, or partially blocked.

19. The method of claim 18, wherein temporally processing the thermographic data includes:
detrending and squaring time domain signals of the thermographic data for the cooling holes;
applying a highpass filter to the thermographic data that has been detrended and squared; and
calculating a signal to noise ratio of the thermographic data that has been squared and detrended and after the highpass filter is applied.

20. The method of claim 18, wherein the spatial scores are calculated based on a fraction of pixels in the thermographic data associated with each of the cooling holes having at least a designated temperature response within a designated area around the cooling hole.

21. The method of claim 18, further comprising opening one or more of the cooling holes that is determined to be blocked or partially blocked.

* * * * *